(12) United States Patent
DiMauro et al.

(10) Patent No.: US 7,399,742 B2
(45) Date of Patent: Jul. 15, 2008

(54) ANTI-OSTEOLYTIC THERAPY INVOLVING ADIPONECTIN

(75) Inventors: Thomas M. DiMauro, Southboro, MA (US); Mohamed Attawia, Canton, MA (US); Hassan Serhan, South Easton, MA (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 11/018,438

(22) Filed: Dec. 21, 2004

(65) Prior Publication Data

US 2006/0019889 A1 Jan. 26, 2006

Related U.S. Application Data

(63) Continuation-in-part of application No. 10/938,903, filed on Sep. 10, 2004.

(60) Provisional application No. 60/590,526, filed on Jul. 23, 2004.

(51) Int. Cl.
*A61K 38/19* (2006.01)
(52) U.S. Cl. ............................ 514/2; 530/324; 530/350
(58) Field of Classification Search ...................... 514/2; 530/324, 350, 356
See application file for complete search history.

(56) References Cited

U.S. PATENT DOCUMENTS

| | | | |
|---|---|---|---|
| 3,805,776 A * | 4/1974 | Thiele | 606/60 |
| 3,886,948 A | 6/1975 | Hakim | |
| 3,924,000 A * | 12/1975 | Thiele | 514/560 |
| 4,332,255 A | 6/1982 | Hakim et al. | |
| 4,387,715 A | 6/1983 | Hakim et al. | |
| 4,439,202 A * | 3/1984 | Sernaker | 8/471 |
| 4,551,128 A | 11/1985 | Hakim et al. | |
| 4,595,390 A | 6/1986 | Hakim et al. | |
| 4,615,691 A | 10/1986 | Hakim et al. | |
| 4,772,257 A | 9/1988 | Hakim et al. | |
| 4,816,016 A | 3/1989 | Schulte et al. | |
| 5,176,627 A | 1/1993 | Watson | |
| 5,282,864 A | 2/1994 | Noiles et al. | |
| 5,869,330 A * | 2/1999 | Scherer et al. | 435/320.1 |
| 5,928,182 A | 7/1999 | Kraus et al. | |
| 6,083,912 A * | 7/2000 | Khouri | 514/12 |
| 6,083,919 A | 7/2000 | Johnson et al. | |
| 6,328,765 B1 * | 12/2001 | Hardwick et al. | 623/23.72 |
| 6,352,557 B1 | 3/2002 | Ferree | |
| 6,419,944 B2 | 7/2002 | Tobinick | |
| 6,503,507 B1 | 1/2003 | Allen | |
| 6,527,759 B1 | 3/2003 | Tachibana et al. | |
| 6,579,852 B2 * | 6/2003 | Fruebis et al. | 514/12 |
| 6,592,888 B1 | 7/2003 | Jensen et al. | |
| 6,605,751 B1 | 8/2003 | Gibbins et al. | |
| 2002/0026244 A1 | 2/2002 | Trieu | |
| 2002/0132773 A1 * | 9/2002 | Kincade et al. | 514/12 |
| 2003/0039651 A1 | 2/2003 | Olmarker | |
| 2003/0049256 A1 | 3/2003 | Tobinick | |
| 2003/0125679 A1 | 7/2003 | Kubota et al. | |
| 2003/0204229 A1 | 10/2003 | Stokes | |
| 2004/0193274 A1 | 9/2004 | Trieu | |
| 2004/0241802 A1 * | 12/2004 | Kadowaki et al. | 435/69.1 |
| 2005/0048644 A1 | 3/2005 | Hedrick et al. | |

FOREIGN PATENT DOCUMENTS

| | | | |
|---|---|---|---|
| EP | 0990924 | | 4/2000 |
| GB | 001243223 | * | 8/1971 |
| WO | WO 02/100387 A1 | | 12/2002 |
| WO | WO 2005/049055 A | | 6/2005 |

OTHER PUBLICATIONS

Wolf, Anna (Biochemical and Biophysical Research Communications 323 (2) 630-5, 2004.*
Yang S-Y (Gene Therapy 11 (5) 483-91, 2004).*
Carmody Emily E (Arthritis and Rheumatism 46 (5) 1298-308, 2002).*
Goodman Stuart (J Biomed Mater Res A, 65 (1) 43-50, 2003).*
Eaton, Medicine & Health, Rhode Island 87, 201-4, 2004.*
March, Medical Journal of Australia 180, S6-S10, 2004.*
Carmody et al., Arthritis & Rheumatism, *Viral Interleukin-10 Gene Inhibition of Inflammation, Osteoclastogenesis* . . . , vol. 46(5), May 2002, pp. 1298-1308.
Goodman et al., JBMR, *Modulation of Bone Ingrowth and Tissue Differentiation by Local Infusion of Interleukin-10* . . . , 2002, pp. 43-50.
Hart et al., Immunology, *Comparison of the Suppressive Effects of Interleukin-10 and Interleukin-4 on Synovial Fluid Macrophages*. . . , 84, 1995, pp. 536-542.
Hughes et al., Rheumatology, *Interleukin 10 and Arthritis*, 38, 1999, pp. 293-297.
Pollice et al., J. of Orthop. Res., *Interleukin-10 Inhibits Cytokine Synthesis in Monocytes Stimulated by Titanium Particles*. . . ,, vol. 16(6), 1998, pp. 697-704.
Trindade et al., Biomaterials, *Interleukin-10 Inhibits Polymethylmethacrylate Particle Induced Interleukin-6* . . . , 22, 2001, pp. 2067-2073.
Alini, Eur. Spine J., *A Biological Approach to Treating Disc Degeneration: Not for Today, but Maybe for Tomorrow*, 11 (Supp. 2), 2002, pp. S215-220.
Ardehali, J. Biomed,, *The Inhibitory Activity of Serum to Prevent Bacterial Adhesion is Mainly Due to Apo-transferrin*, Mat, Res., Jul 1, 2003, 66, 1, pp. 21-28.
Cassatella, *J. Exp. Med. Interleukin 10 (IL-10) Inhibits the Release of Proinflammatroy Cytokines* . . . , Dec. 1, 1993, 178(6), pp. 2207-2211.
Cassatella, *J. Exp. Med., Interleukin 10 (IL-10) Upregulates IL-1 Receptor Antagonist Production* . . . , May 1, 1994, 179(5) pp. 1695-1699.

(Continued)

*Primary Examiner*—David Lukton

(57) ABSTRACT

This invention is directed to administering an effective amount of adiponectin into an osteolytic region for treating osteolysis.

10 Claims, 10 Drawing Sheets

OTHER PUBLICATIONS

Desai, *Anal. Biochem., Coated Microwell Plate-based Affinity Purification of Antigens*, May 15, 2004, 328(2), pp. 162-165.

Diez, *Eur. J. Endocrinology, The Role of the Novel Adipocyte-derived Hormone Adiponectin in Human Disease*, 2003, 148, pp. 293-300.

Goupille, *Spine, Matrix Metalloproteinases: The Clue to Intervertebral Disc Degeneration?*, 23(14), 1998, pp. 1612-1626.

Guillen, *Arthritis, Rheum., The Effects of Local Administration of Lactoferrin on Inflammation in Murine Autoimmune and Infectious Arthritis*, 43, 2000, pp. 2073-2780.

Hayashida, *Eur. J. Pharmacology, Lactoferrin Enhances Peripheral Opioid-mediated Antinociception via Nitric Oxide in Rats*, 484, 2004, pp. 175-181.

Hayashida, *J. Vet. Med. Sci., Oral Administration of Lactoferrin Inhibits Inflammation and Nociception in Rat Adjuvant-Induced Arthritis*, 66(2), 2004, pp. 149-154.

Karppinen, *Spine, Tumor Necrosis Factor-α Monoclonal Antibody, Infliximab, Used to Manage Severe Sciatia*, 28(8), 203, pp. 750-754.

Kumada, *Circulation, Adiponectin Specifically Increased Tissue Inhibitor of Metalloproteinase-1 Through Interleukin-10. . .*, May 4, 2004, 109(17) pp. 2046-2049.

Matsuda, *J. Biol. Chem., Role of Adiponectin in Preventing Vascular Stenosis*, 277(40) pp. 37487-37491.

Motoshima, *Biochem. Biophys. Res. Comm., Adiponectin Suppresses Proliferation and Superoxide Generation and Enhances eNOS Activity . . .*, 2004, 315, pp. 264-172.

Nakano, *J. Biochem (Tokyo), Isolation and Characterization of GBP28, a Novel Gelatin-Binding Protein Purified from Human Plazma*, Oct. 1996, 120(4), pp. 803-812.

Ohko, *J. Biomed. Mat. Res. (Appl Biomet), Self-Sterilizing and Self-Cleaning of Silicone Catheters Coated with $TiO_2$ Photocatalyst Thin Films: A Preclinical Work*, 58, 2001, pp. 97-101.

Ouichi, *Circulation, Adipocyte-derived Plasma Protein, Adiponectin, Suppresses Lipid Accumulation and Class A Scavenger Receptor Expression, . . .* 103(8), Feb. 27, 2001, p. 1057.

Ouichi, *Circulation, Novel Modulator for Endothelial Adhesion Molecules . . .*, 1999, 100, pp. 2473-2476.

Brakenhielm, *PNAS, Adiponectin-induced Antiangiogenesis and Antitumor Activity Involve Caspase-Mediated Enhothelial Cell Apoptosis*, 101(8), pp. 2476-2481.

Shanbhag, *J. Biomed. Mar. Res., Decreased Neutrophil Respiratory Burst on Exposure to Cobalt-Chrome alloy and Polystyrene in vitro*, vol. 26, 1992, pp. 185-195.

Shimada, *Clin. Chim. Actga. Adiponectin and Atheroscierotic Disease*, Jun. 2004, 344(1-2), pp. 1-12.

Singh, *Nature, A Component of Innate Immunity Prevents Bacterial Biofilm Development*, 417, May 30, 2002, pp. 552-555.

Talukder, *J. Vet. Med. Sci. Receptor-Mediated Transport of Lactoferrin into the Cerebrospinal Fluid via Plasma in Young Calves,*, 65(9), 2003, pp. 957-964.

Taylor, *Regul. Toxicol. Pharmacol. Safety Determination for the use of Bovine Milk-derived Lactoferrin as a Component of an Antimicrobial Beef Carcass Spray*, Feb. 2004, 39(1), pp. 12-24.

Trampuz et al., Clin. Orthop, *Molecular and Antibiofilm Approaches to Prosthetic Joint Infection*, (414), 2003, pp. 69-88.

Trif, Exp. Biol. Med (Maywood), *Liposomes as Possible Carriers for Lactoferrin in the Local Treatment of Inflammataory Diseases*, 226(6), 2001, pp. 559-564.

Tobinick, Swiss Med.Weekly, *Perispinal TNF-alpha Inhibition for Discogenic Pain*, 2003, 133, pp. 170-177.

Wulster-Radcliffe, Biochem, Biophys. Res. Comm., *Adiponectin Differentially Regulates Cytokines in Porcine Macrophages*, 316, 2004, pp. 924-929.

Yamamoto, Biochem. Biophys. Res. Comm., *Effect of Interleukin-10 on the Gene Expression of Type 1 Collagen, Fibronectin, and Decorin in Human Skin Fibroblasts: Differential Regulations by Transforming Growth Factor-β and Monocyte Chemoattractant Protein-1*, 316, 2004, pp. 924-929.

Yokota, *Blood, Adiponectin, a New Member of the Family of Soluble Defense Collagens, Negatively Regulates the Growth of Myelomonocytic Progenitors and the Functions of Macrophages*, Sep. 1, 2000, 96(5), pp. 1723-1732.

Brennan, Rheumatology, *Interleukin 10 and Arthritis*, 38, 1999, pp. 293-297.

Carmody, et al., Arthritis & Rheumatism, *Viral Interleukin-10 Gene Inhibition of Inflammation, . . .*, 46(5), May 2002, pp. 1298-1308.

Goodman et al., *Modulation of Bone Ingrowth and Tissue Differentiation by Local Infusion of Interleukin-10. . .*, JBMR, 65A, 2003, pp. 43-50.

Hart, et al., Immunology, *Comparison of the Suppressive Effects of Interleukin-10 and Interleukin-4 on Synovial Fluid Macrophages . . .*, 84(4), Apr. 1995, pp. 536-542.

Pollice et al., J. Orthop Res., *Interleukin-10 Inhibits Cytokine Synthesis in Monocytes Stimulated by Titanium Particles: . . .*, 16(6), Nov. 1998, pp. 697-704.

Trindade, et al., Biomaterials, *Interleukin-10 Inhibits Polymethylmethacrylate Particle Induced interleukin-6 and . . .*, 22, 2001, pp. 2067-2073.

Maeda, S. et al., Spine, *Changes with Age in Proteoglycan Synthesis in Cells Cultured* in Vitro *from the Inner and Outer Rabbit Annutus Fibrosus*, vol. 25(2), 2000, pp. 166-169.

Schierholz J M et al., "Development of A New CSF-Shunt with Sustained Release of An Antimicrobial Broad-Spectrum Combination", Zentralblatt fur Bakteriologie, Jun. 1997, pp. 107-123, vol. 286, No. 1.

\* cited by examiner

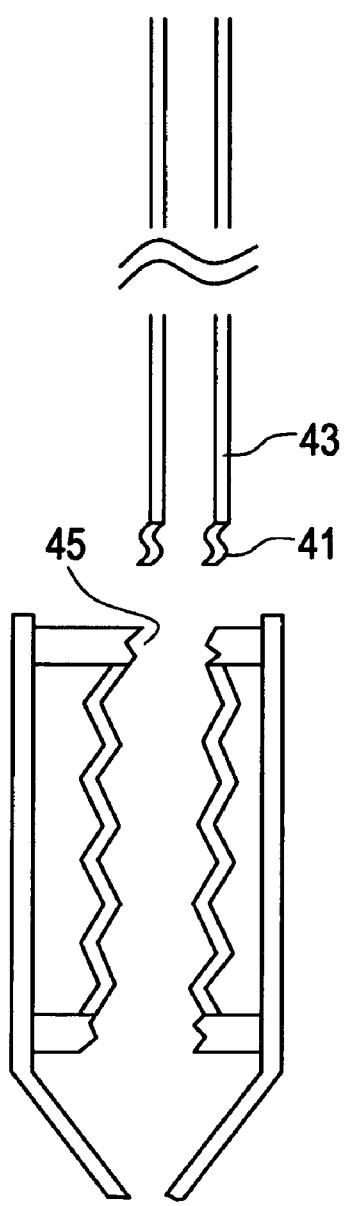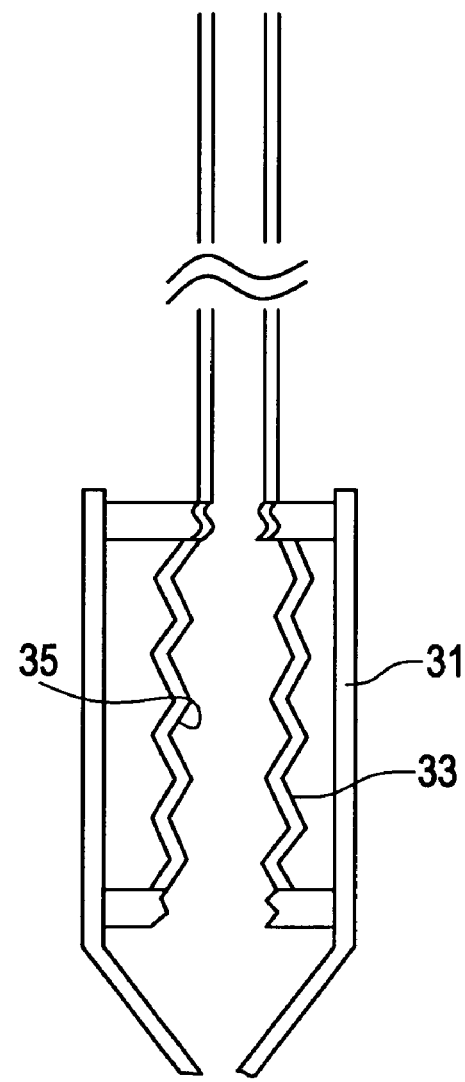

FIG. 5A
FIG. 5B
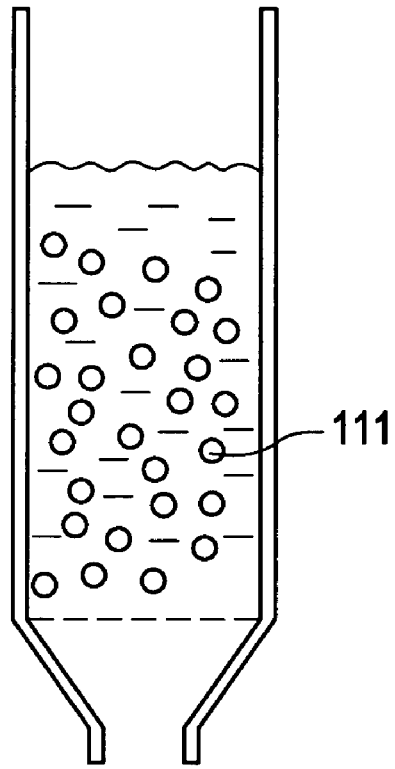
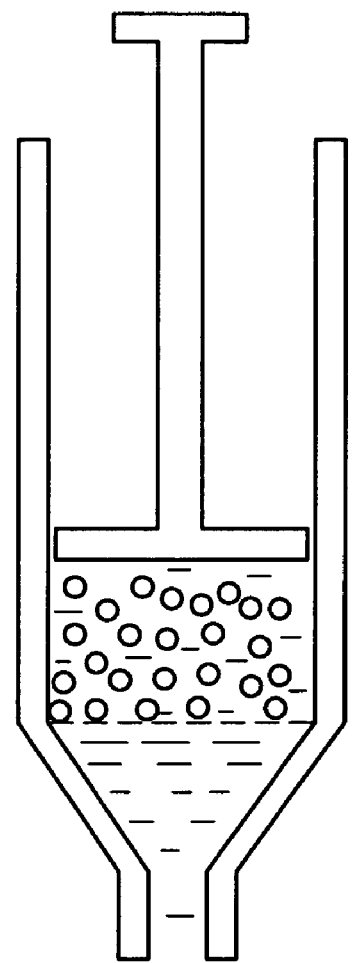

ANTI-OSTEOLYTIC THERAPY INVOLVING ADIPONECTIN

CONTINUING DATA

This application claims the benefit of U.S. Provisional Patent Application Ser. No. 60/590,526, entitled "Intradiscal Anti-Inflammatory Therapy Involving Autologous Adiponectin", DiMauro et al., filed Jul. 23, 2004, and U.S. patent application Ser. No. 10/938,903, entitled "Intradiscal Anti-Inflammatory Therapy Involving Autologous Adiponectin", DiMauro et al., filed Sep. 10, 2004, the specifications of which are incorporated by reference in its entirety.

BACKGROUND OF THE INVENTION

Minute particles emanating typically due to wear and typically from either ultra high molecular weight polyethylene ("UHMWPE") interfaces or polymethylmethacrylate ("PMMA") cement cause an inflammatory immune response resulting in osteolysis (i.e., dissolution or degeneration of bone tissue). Osteolysis is believed to be a primary causes of implant revision in hip and knee implants. It is believed the method of the present invention is applicable to other implants that are susceptible to the above described mechanism of inflammatory immune response resulting in osteolysis including other artificial joints such as spinal discs.

SUMMARY OF THE INVENTION

The present inventors have developed a number of procedures for efficaciously treating osteolysis by therapy involving adiponectin ("APN"). In some embodiments, APN is injected in a therapeutic amount around or into a prosthetic implant causing osteolysis. In others, APN is combined with viable cells to produce at least one anti-inflammatory compound selected from tissue inhibitor of MMP-1 ("TIMP-1") and interleukin-10 ("IL-10"), and the anti-inflammatory compound is then injected periprosthetically.

Therefore, there is provided a method of treating osteolysis, comprising the steps of:
  a) periprosthetically administering an effective amount of a formulation comprising adiponectin (APN).

It is believed that adiponectin is strongly anti-inflammatory. In particular, it is believed that APN upregulates certain anti-inflammatory molecules (e.g., TIMP-1, IRAP and IL-10) and downregulates certain pro-inflammatory molecules (e.g., TNF-α, IL-6 and ROS).

The literature appears to recognize the strong anti-inflammatory nature of APN. Shimda reports that adiponectin has protective actions in the initiation and progression of atherosclerosis through anti-inflammatory and anti-atherosclerotic effects." Shimada, Clin. Chim. Acta, 2004, June 344(1-2):1-12. Yokota indicates that adiponectin is involved in the termination of inflammatory responses, and suggests that adiponectin may have therapeutic applications in diseases caused by excessive inflammatory responses."Yokota, Blood, 1 Sep. 2000 96(5), 1723-1731. Diez concludes that the ability of adiponectin to increase insulin sensitivity in connection with its anti-inflammatory and anti-atherogenic properties have made this novel adipocytokine a promising therapeutic tool for the future". Diez, Eur. J. Endocrinology (2003) 148, 293-300.

APN antagonizes TNF-α. Yokota, Blood, 2000, September 1, 96(5), 1723-32 reports that about 10 µg APN/l (check units) inhibits phagocytic activity and completely eliminates TNF-α production from LPS-induced phagocytes. In particular, Yokota reported that LPS-induced production of TNF-α in human macrophages dropped from over 800 µg/ml TNF-α to less than 20 µg/ml TNF-α when only 10 µg/l APN was applied. Yokota concluded that APN is an important negative regulator of immune systems, may be a unique suppressor of inflammatory responses because of its specific inhibition of TNF-α transcription, may be involved in ending inflammatory responses, and may have therapeutic applications in diseases caused by excessive inflammation.

Wulster-Radcliffe, Biochem. Biophys. Res. Comm., 316 (2004), pp. 924-929, also reports that pretreatment of human macrophages with 10 µg/ml APN suppressed TNF-α production by about 50%, and hypothesized that some of the anti-inflammatory actions thereof are mediated in part by APN suppression of NFκB signaling and ERK1/2 activity.

Therefore, in some embodiments, the APN is directly injected periprosthetically into a osteolytic region, preferably in an amount sufficient to antagonize TNF-α. More preferably, it further antagonizes IL-6 and ROS. Accordingly, there is provided a method of treating osteolysis, comprising periprosthetically administering an effective amount of a formulation comprising APN into an osteolytic region.

In some embodiments, the APN may be autologous, while in others it may be exogenous. When exogenous APN is selected, it is preferably recombinant.

APN upregulates TIMP-1. For example, Kumada, Circulation, 2004, May 4, 109(17) 2046-9 reports that APN indirectly increases the concentration of tissue inhibitor of MMP-1 ("TIMP-1") through IL-10 upregulation when combined with human macrophage monocytes.

Therefore, in another embodiment, viable cells and APN are cultured ex vivo to produce TIMP-1, and an effective amount of the TIMP-1 is then injected into the osteolytic region. In particular embodiments, there is a method of treating inflammation wherein viable cells capable of inducibly expressing TIMP-1 are cultured in the presence of an TIMP-1-inducing agent to produce an effective amount of TIMP-1. The TIMP-1 is then injected into the osteolytic region. This method is advantageous in that sufficient ex vivo production of TIMP-1 is insured by the clinician's ability to provide as much time as is needed to produce a sufficient quantity of TIMP-1.

Therefore, in accordance with the present invention, there is provided a method of treating osteolysis, comprising the steps of:
  a) obtaining from the patient cells viable capable of producing TIMP-1;
  b) mixing an TIMP-1-inducing composition with the viable cells for a period sufficient to produce TIMP-1, and
  c) periprositheitcally administering an effective amount of a formulation comprising TIMP-1 into an osteolytic region.

In other embodiments, adiponectin is combined ex vivo with viable cells capable of expressing TIMP-1, and this mixture is then injected into the osteolytic region and thereafter produces in vivo an effective amount of TIMP-1 within the osteolytic region inside the disc. In particular embodiments, there is a method of treating inflammation wherein viable cells that are capable of producing TIMP-1 are mixed with an TIMP-1-inducing agent and then are injected into an osteolytic region, whereby the inducable cells thereafter produce in vivo an effective amount of TIMP-1. This method is advantageous in that sufficient in vivo production of TIMP-1 is insured by the clinician's ability to provide as many viable cells as is needed to produce an effective amount of TIMP-1.

Moreover, since the cells are injected prior to induction, there is no need to wait for an ex vivo incubation period.

Therefore, in accordance with the present invention, there is provided a method of administering TIMP-1 to a patient, comprising:
 a) obtaining from the patient cells viable capable of producing TIMP-1;
 b) mixing an TIMP-1-inducing composition with the viable cells for a period sufficient to produce induced cells, and
 c) administering the induced cells to a location in the patient, whereby the induced cells in vivo produce TIMP-1 at the location.

Wulster-Radcliffe, *Biochem. Biophys. Res. Comm.*, 316 (2004), pp. 924-929, also further reports that pretreatment of human macrophages with 10 µg/ml APN suppressed IL-6 production by about 50%, and concluded that the anti-inflammatory properties of APN should extend to negative regulation of IL-6 as well.

Kumada has linked APN to the upregulation of IL-10. Kumada, supra, hypothesizes that APN increases the TIMP-1 level through IL-10 expression.

Wulster-Radcliffe, *Biochem. Biophys. Res. Comm.*, 316 (2004), pp. 924-929, also further reports that pretreatment of human macrophages with 10 µg/ml APN induced IL-10 production, and concluded that APN upregulates IL-10.

IL-10 has also been reported to be a potent anti-inflammatory molecule. For example, Cassatella, *J. Exp. Med.*, 1993, Dec. 1, 178(6) 2207-11, reports that IL-10 inhibits the release of pro-inflammatory cytokines. Cassatella, *J. Exp. Med.*, 1994 May 1, 179(5) 1695-9, reports that IL-10 upregulates IRAP in neutrophils. According to Brennan, *Rheumatology* 1999, 38, 293-7, IL-10 can induce the production of cytokine inhibitors, including the IL-1 receptor antagonist (IL-Ira) and the release of both soluble TNF receptors p55 and p75 in monocytes. Because of this utility, Brennan chartacterizes IL-10 as a 'macrophage deactivating factor'. According to Hart, *Immunology*, 1995, April 84 (4) 536-42, IL-10 and IL-4 have the capacity to downregulate both pro-inflammatory molecules TNF-a and IL-1β.

It is further known that Il-10 is particularly suited for treating osteolysis. It is believed that IL-10 possesses a number of features (including antagonism of osteoclasts) that make it an attractive therapeutic agent for treating or preventing osteolysis.

Pollice *J. Orthop. Res.* 1998 Nov. 16(6) 697-704 discloses that IL-10 inhibits inflammatory cytokine synthesis by monocytes stimulated with titanium particles. Trindade, *Biomaterials* 22 (2001) 2067-73 discloses that IL-10 inhibits PMMA-induced IL-6 and TNF-a release by human monocytes/macrophages in vitro. Goodman, *JBMR*, 65A:43-50, 2003 used a small infusion pump to continuously provide IL-10 to a site contaminated with UHMWPE particles and found that local infusion of immune-modulating cytokines such as IL-10 may prove to be useful in abating particle-induced periprosthetic osteolysis. Carmody, *Arthritis & Rheumatism*, 46(5) May 2002 pp. 1298-1308 teaches viral IL-10 gene inhibition of inflammation, osteoclastogenesis and bone resorption in response to titanium particles.

Since IL-10 is a strong anti-inflammatory, anti-osteolytic molecule induced by APN, the present invention also contemplates the direct injection of APN-induced IL-10 as well. Therefore, in another embodiment, viable cells and APN are cultured ex vivo to produce an effective amount of IL-10, and the IL-10 is then injected into the osteolytic region. In particular embodiments, there is a method of treating osteolysis wherein viable cells capable of inducibly expressing IL-10 are cultured in the presence of an IL-10-inducing agent (such as APN) to produce IL-10. The IL-10 is then injected into the osteolytic region. This method is advantageous in that sufficient ex vivo production of IL-10 is insured by the clinician's ability to provide as much time as is needed to produce a sufficient quantity of IL-10.

Therefore, in accordance with the present invention, there is provided a method of treating osteolysis, comprising the steps of:
 a) obtaining from the patient cells viable capable of producing IL-10;
 b) mixing an IL-10-inducing composition (preferably comprising adiponectin) with the viable cells for a period sufficient to produce a formulation comprising IL-10, and
 c) periprosthetically administering an effective amount of the formulation comprising IL-10 into an osteolytic region.

In other embodiments, adiponectin is combined ex vivo with viable cells capable of expressing IL-10. This mixture is then injected into the osteolytic region and thereafter produces an effective amount of interleukin-10 inside the osteolytic region. In particular embodiments, there is a method of treating inflammation wherein viable cells that are capable of producing IL-10 are mixed with an IL-10-inducing agent and then are injected into an osteolytic region, whereby the inducable cells thereafter produce in vivo an effective amount of IL-10. This method is advantageous in that sufficient in vivo production of interferon is insured by the clinician's ability to provide as many viable cells as is needed to produce an effective amount of IL-10. Moreover, since the cells are injected prior to induction, there is no need to wait for an ex vivo incubation period.

Therefore, in accordance with the present invention, there is provided a method of administering IL-10 to a patient, comprising:
 a) obtaining from the patient cells viable capable of producing IL-10;
 b) mixing an IL-10-inducing composition with the viable cells for a period sufficient to produce induced cells, and
 c) administering the induced cells to an osteolytic region in the patient, whereby the induced cells in vivo produce IL-10 at the osteolytic region.

It has been further noted by the present inventors that osteolysis is generally associated with very large macrophage concentrations. Accordingly, the osteolytic region may already possess a sufficient amount of cells capable of producing IL-10 such that there is no need to independently obtain viable cells from the patient for the purpose of producing IL-10. Rather, the clinician need only inject APN into the osteolytic region and rely upon the combination of the APN with local macrophages to locally produce an effective amount of IL-10.

Therefore, in accordance with the present invention, there is provided a method of treating osteolysis, comprising the steps of:
 a) obtaining a formulation comprising APN (preferably autologous APN), and
 b) periprosthetically administering an effective amount of the formulation comprising APN into an osteolytic region.

It is further believed that APN has anti-oxidant capabilities. Motoshima, *Biochem. Biophys. Res. Comm.*, 315 (2004) 264-172 reports that the global component of APN suppresses cellular superoxide generation in endothelial cells treated with oxidized LDL. Accordingly, it is believed that the application of APN to an osteolytic region would have the further effect of antagonizing the reactive oxygen species (ROS) therein.

Therefore, it appears that APN holds a special advantage as a therapeutic compound in treating osteolysis in that it not only is a potent anti-inflammatory molecule that can strongly antagonize a key pro-inflammatory lynchpin of osteolysis (TNF-α), APN also induces the production of two key anti-inflammatory proteins (TIMP-1 and IL-10), one of which (IL-10) is also antagonistic towards osteoclasts.

DESCRIPTION OF THE FIGURES

FIGS. 3a-3e are cross-sections of the use of a bellows-type syringe in accordance with the present invention.

FIGS. 5a-5b are cross-sections of a syringe of the present invention having a collagen particles therein for separating APN from plasma.

DETAILED DESCRIPTION OF THE INVENTION

Figure 1:
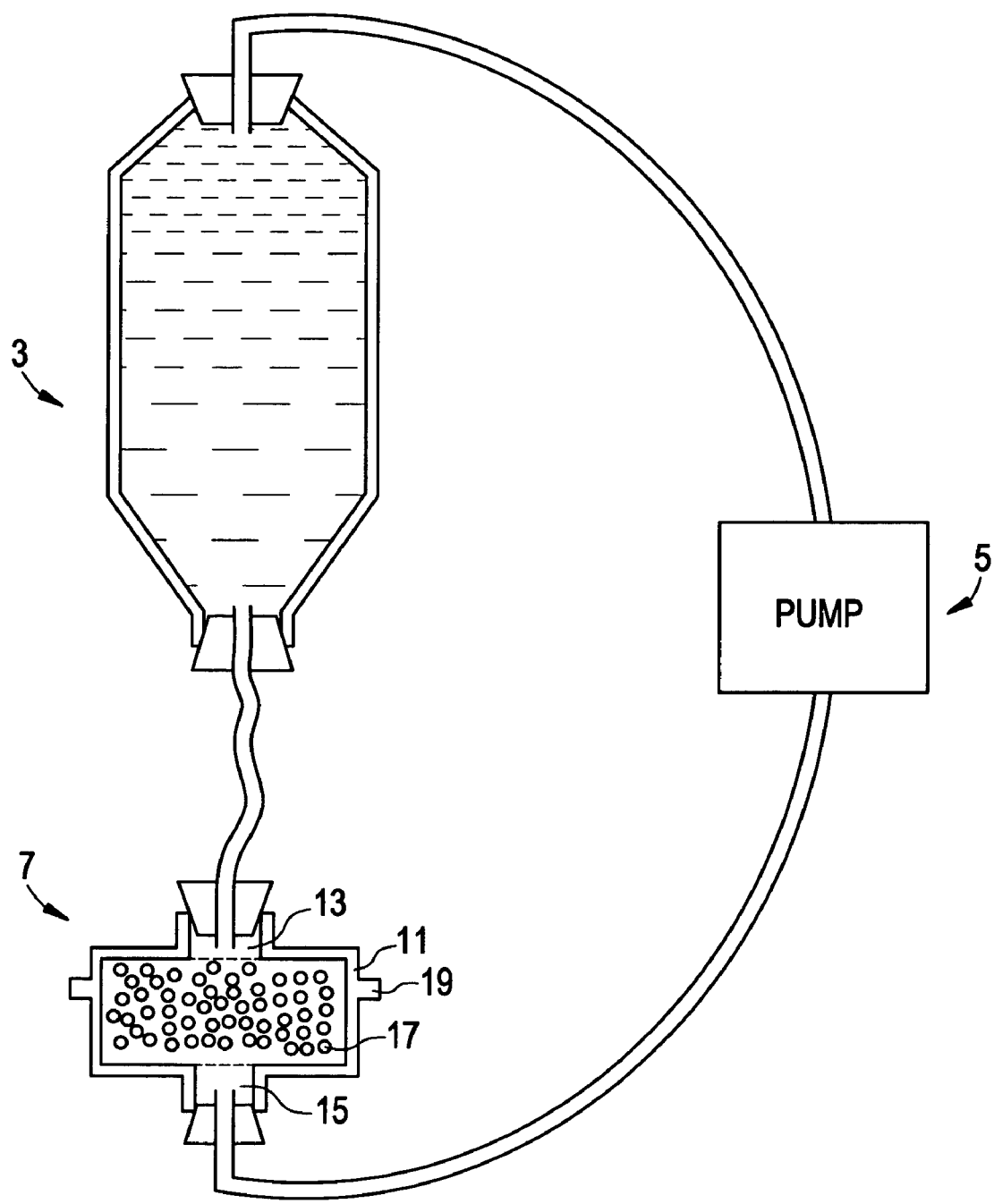
FIG. 1 is a schematic of an APN separation system.

Ouichi, *Circulation*, 103(8), 2001, Feb. 27, p. 1057 has reported that APN is present in an abundance in whole blood, typically accounting for 0.01% of the protein content of human blood. Therefore, in preferred embodiments, APN is preferably obtained from the whole blood of the patient, as it is present there in large amounts.

In one particularly preferred embodiment, whole blood obtained from the patient is centrifuged to provide a plasma portion. It has been reported by Yokota, supra, that APN levels in plasma of healthy humans ranges from 1.9-17.0 µg/ml. Since it has been reported by Yokota that the inhibitory effect of APN upon TNF-α was seen at about 5 µg/ml, it is noted that unconcentrated plasma may likely possess levels of APN that are therapeutically effective in stopping osteolysis-associated inflammation.

Therefore, in some embodiments, there is provided a method of treating osteolysis, wherein a formulation consisting essentially of plasma comprising an effective amount of APN is injected into the osteolytic region. In some embodiments thereof, an APN-rich portion of the plasma is obtained, for example, by using a gradient fluid with a centrifuge, and then injecting that APN-rich fraction into the osteolytic region.

In some embodiments, the plasma may be centrifuged in a container having a plurality of side ports. A needle may be passed through one of these side ports to access the APN-rich layer of the plasma.

In some embodiments, the plasma portion is separated from the remainder of the blood and passed through an affinity column containing a separation material for which APN has a high affinity. The APN is thus preferentially adsorbed onto the separation material. Next, adsorbed APN is eluted from the separation material using a suitable elution solution.

Nakano, *J. Biochem* (*Tokyo*), 1996 October 120(4) 803-12, examined methods for isolating APN, and found not only that APN binds specifically to gelatin, but also that it can be eluted from the gelatin material by a 1M NaCl solution. Nakano further reported that applying these methods to 500 ml of human plasma resulted in the isolation of about 50 µg of APN.

Therefore, in preferred embodiments, the plasma portion is separated from the remainder of the blood and passed through an affinity column containing gelatin (or collagen I, III or V), and the adsorbed APN is eluted from the column using a 1 M NaCl solution.

In other embodiments, APN may be separated from the collagen by digesting the collagen with, for example, trypsin or collagenase.

In other embodiments, APN is obtained from adipose tissue, as it is exclusively released by adipose tissue.

In other embodiments, other conventional separation procedures may be used to separate APN from the other components of whole blood or fat.

Once the APN has been isolated, it is, in some embodiments, combined with viable cells either in vivo or ex vivo. These combinations are provided in order to induce production of an effective amount of at least one of IL-10, TIMPs-1, and mixtures thereof.

In preferred viable cell embodiments thereof, a physiologic fluid containing viable leucocyte cells is obtained from the patient. Preferably, the physiologic fluid is derived from whole blood. Whole blood contains monocytes capable of producing IL-10 or TIMP-1 and is easily obtainable from the patient. More preferably, the whole blood is then fractionated by a conventional procedure (such as centrifugation or filtration) to obtain a selected portion of whole blood having a relatively high concentration of monocytes or neutrophils.

In some embodiments, the leucocytes are derived from the buffy coat fraction of whole blood. The buffy coat typically comprises about 5-10 vol % of whole blood. Utilization of the buffy coat in the present invention is desirable because it contains a concentrated amount of monocytes capable of producing autologous IL-10 or TIMP-1. Typically, the concentration of monocytes will be on the order of 10-20 fold over that found in whole blood. In some embodiments, a portion of the buffy coat may be used.

In other embodiments, the buffy coat is combined with other portions of blood in order to exploit desirable properties of molecules present in the other portions of blood.

For example, in some embodiments, the buffy coat is combined with at least a portion of the plasma fraction. The plasma fraction contains fibrinogen and so may be useful for clotting the inducing composition to insure that the induced cells that are injected periprosthetically remain in the osteolytic region, or for forming a sustained release device for APN, IL-10 or TIMP-1.

In other embodiments, the buffy coat is combined with thrombin in order to produce clotting.

In some embodiments, the buffy coat is combined with at least a portion of the platelet fraction of the blood. The platelet fraction contains growth factors such as TGF-β, which, upon release, can help stimulate extra cellular matrix production by natural disc cells.

It is further known in the art that osteolysis is characterized not only by the presence of macrophages, but also by the presence of lymphocytes. Since it is also known that lymphocytes may secrete pro-inflammatory cytokines via the Th1 pathway, it is appropriate to consider the activity of these cells in osteolytic therapies.

U.S. Pat. No. 6,083,919 (Johnson) has reported that co-administration of IL-10 and TGF-β in amounts effective to produce a synergistic reduction in lymphocyte activity. In one example, Johnson reports that about 0.3 ng/ml of each of IL-10 and TGF-β inhibits the activation of self-reactive T cells in autoimmune diseases from 20,000 units to less than 500 units.

Therefore, in accordance with the present invention, there is provided a method of treating osteolysis, wherein both APN and TGF-β are periprosthetically admininstered in amounts effective to produce a synergistic reduction in lymphocyte activity.

Also in accordance with the present invention, there is provided a method of treating osteolysis, wherein both IL-10 and TGF-β are periprosthetically admininstered in amounts effective to produce a synergistic reduction in lymphocyte activity.

In one embodiment of the present invention, effective amounts of TGF-β can be obtained by activation of platelet-rich plasma (PRP). Preferably, the TGF-β is administered to provided an effective concentration of at least 1 ng/ml.

Conventional protein production technology may be exploited to include a number of unit processes designed to partially purify the concentration of APN. Such conventional processes include the use of glass beads to capture the APN; the use of a 10 kD filter to capture the APN; the use of a molecular sieve to dewater the plasma; the use of ammonium sulfate to precipitate out the APN; and the use of ethanol extraction to precipitate out the APN.

It is reasonable to expect that adoption of at least one of the partial purification techniques described above will lead to a 5-10 fold increase in the APN concentration in the partially purified solution.

In some embodiments, monoclonal antibodies may be used to separate the adiponectin from the rest of the plasma.

It is believed that as little as about 5 μg/ml APN is an effective anti-inflammatory concentration. Greater amounts are generally believed to produce greater anti-inflammatory effects.

Accordingly, in some embodiments of the present invention, the formulation comprises at least 5 μg APN/ml, preferably the formulation comprises at least 10 μg APN/ml, more preferably at least 20 μg/ml, and more preferably at least 30 μg APN/ml.

In some embodiments, the APN or induced cells may be combined with a sustained release device in order to insure a continued presence of the APN or cells in the osteolytic region. In some embodiments, autologous cryoprecipitated fibrinogen is used to make the sustained release device. Cryoprecipitated fibrin may be used as a carrier for APN. In one embodiment, cryoprecipitated fibrinogen is taken from the patient's blood (that could be donated before surgery or even collected during surgery with a Cell-Saver). With autologous fibrin, there would be no risk of rejection since the fibrin is from the patient's own blood proteins. The addition of thrombin to the cryoprecipitate creates a stable gel. With time, the cryoprecipitated fibrin may be replaced with a fibrocartilage-like material, similar to that of the host tissue Therefore, in accordance with the present invention, there is provided a method of treating osteolysis, comprising periprosthetically administering an effective amount of a formulation comprising a APN and fibrin glue having a fibrinogen concentration of at least 10 mg/ml into a osteolytic region, preferably at least 20 mg/ml.

In some embodiments, the APN of this invention is directed against osteolysis occurring due to wear debris (typically UHMWPE wear debris) from a hip joint prosthesis (preferably an acetabular cup). In some embodiments thereof, the acetabular cup is selected from the cups disclosed in U.S. Pat. No. 5,282,864, the specification of which is incorporated by reference in its entirety.

Therefore, in some embodiments, there is provided a kit for treating osteolysis, comprising:
a) an UHMWPE liner for an acetabular cup, and
b) a formulation comprising an effective amount of adiponectin effective for treating osteolysis.

In some embodiments, the APN of this invention is directed against osteolysis occurring due to wear debris (typically UHMWPE wear debris) from a knee joint prosthesis (preferably a tibial insert upon a tibial tray).

Therefore, in some embodiments, there is provided a kit for treating osteolysis, comprising:
a) an UHMWPE insert for a tibial tray, and
b) a formulation comprising an effective amount of adiponectin effective for treating osteolysis.

In some embodiments, the APN of this invention is directed against lysis occurring due to wear debris (typically UHMWPE wear debris) from an intervertebral motion disc prosthesis (typically a cervical motion disc). In some embodiments, an injection of APN is provided when the osteolysis occurs. In some embodiments, the APN is provided in the form of an bio-erodable coating upon the implant at the time of implantation, whereby the APN is slowly released from the coating.

Therefore, in some embodiments, there is provided a kit for treating osteolysis, comprising:
a) an UHMWPE insert for an intervertebral motion disc, and
c) a formulation comprising an effective amount of adiponectin effective for treating osteolysis.

In some embodiments, adjunct materials disclosed in U.S. patent application No. Pub No. 2004/0229878, filed Jul. 31, 2003, "Transdiscal Administration of Specific Inhibitors of p38 Kinase" (DEP5144), the specification of which is incorporated by reference in its entirety, are provided along with the APN.

In some embodiments, the affinity column used to isolate APN is provided as a cartridge. Now referring to FIG. 1, there is provided a separation system 1 for isolating APN, comprising a blood or plasma receptacle 3, a pump 5 and a separation cartridge 7. The separation cartridge comprises a housing 11 having a first open end 13, a second open end 15, and an affinity material 17 housed therein. In some embodiments, the cartridge also has flanges 19 extending from the housing.

In use, blood or plasma is pumped in a closed circuit from the receptacle through the cartridge, through the pump and back to the receptacle. Once the APN has been sufficiently isolated upon the affinity material, the cartridge is removed from the separation system.

Figure 2:
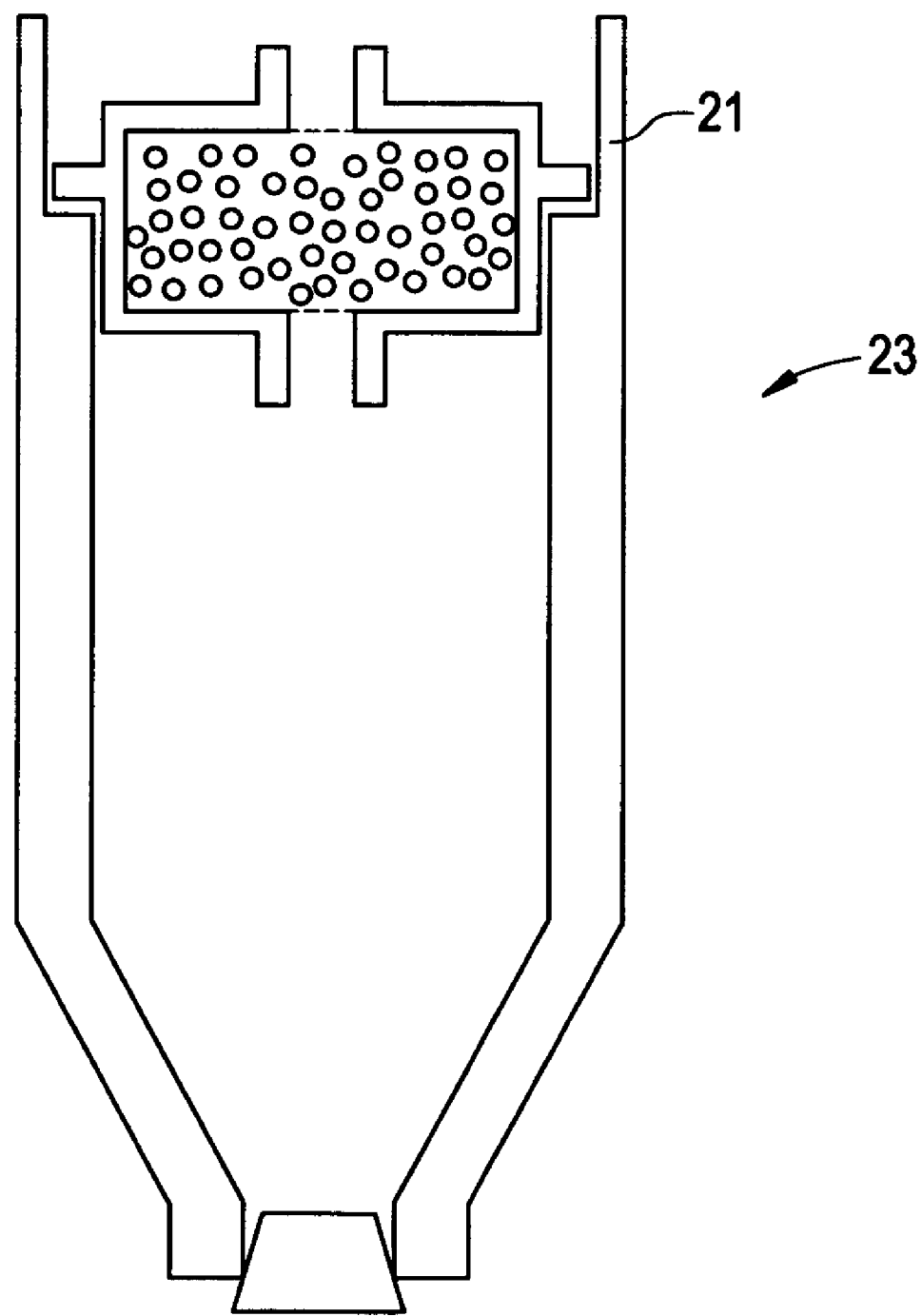
FIG. 2 is a cross-section of an APN-filled cartridge housed within a syringe.
Figure 3C:
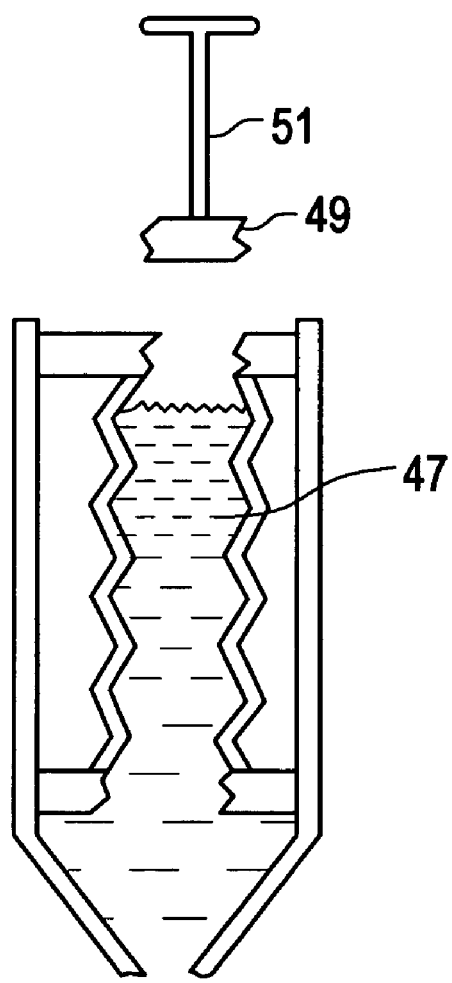
Figure 3D:
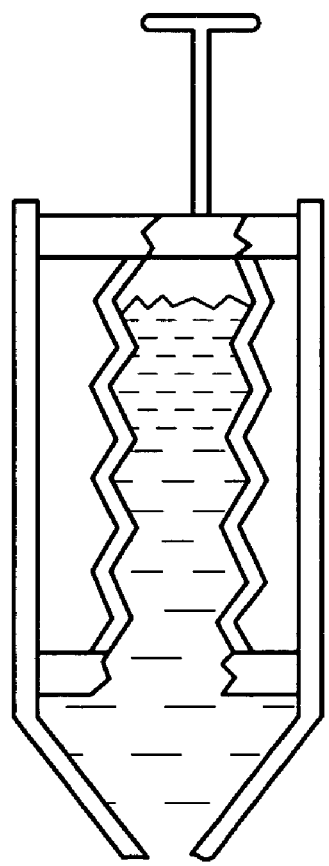
Figure 3E:
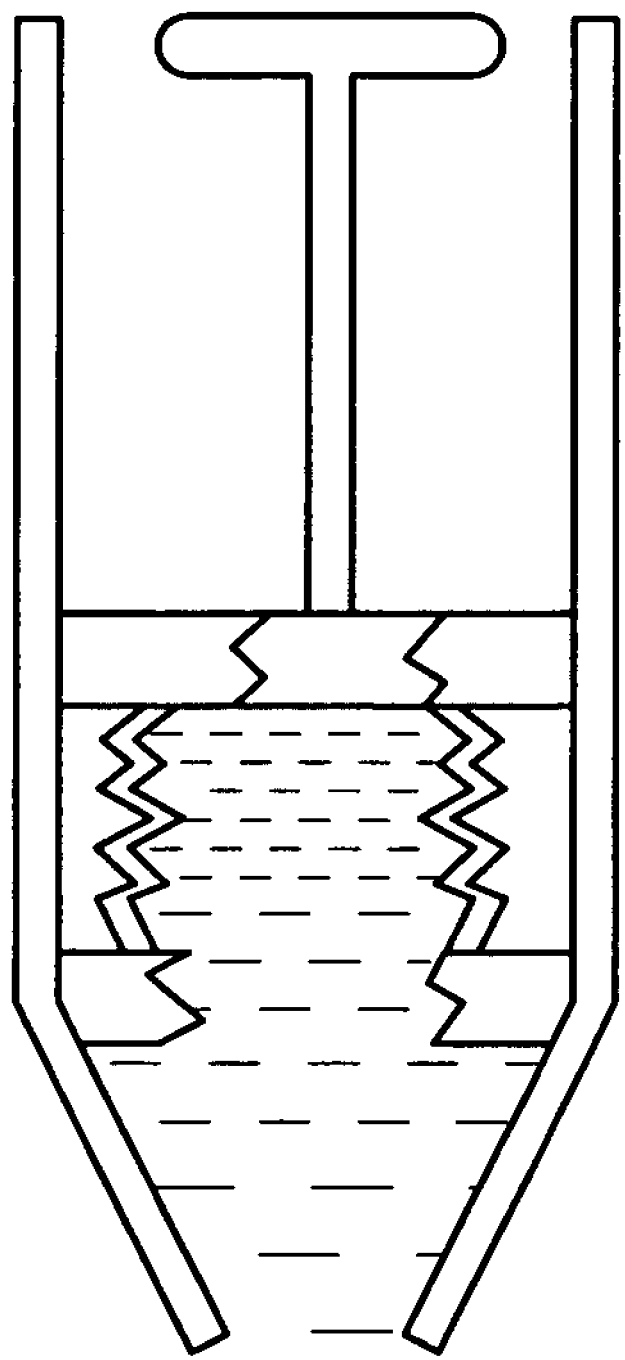

In order to transfer the APN to a syringe for injection, in some embodiments, the cartridge containing the APN is fitted to the proximal end portion 21 of a syringe 23, as in FIG. 2. In this particular embodiment, the flanges of the cartridge fit into mating recesses within the syringe.

Therefore, in accordance with the present invention, there is provided a kit for collecting and administering adiponectin, comprising:
i. a syringe having a barrel having an inner wall, a proximal open end and a distal open end, and ii. a cartridge having a barrel having an inner wall defining a housing, an outer wall, a proximal open end and a distal open end, wherein the outer wall of the cartridge is adapted to fit within the inner wall of the syringe, and iii. an adiponectin-binding agent disposed within the housing.

The APN is then eluted into the syringe with a suitable elutant.

Therefore, in accordance with the present invention, there is provided a syringe having a barrel having an inner wall, a proximal open end and a distal open end, wherein the barrel contains an effective amount of adiponectin.

If the isolated APN is to be injected directly into the osteolytic region, then, now referring to FIGS. 3a-3e, in some embodiments, a device may be used that is adapted to be both a cartridge in the isolation step and a syringe for the injection step. In one embodiment, the device is designed as a conventional syringe 31 modified with a bellows 33. The inner surface 35 of the bellows is coated with the separation material (not shown) (preferably, collagen I, III or V or a gel Cellulofine™) having a high affinity for APN. Now referring to FIGS. 3a-3b, during the APN separation step, a threaded end 41 of a tubing 43 is threaded into the proximal threaded end 45 of the bellows in order to obtain a secure fitting. Blood or plasma is then passed from the tubing into the bellows, wherein the APN preferentially adsorbs onto the separation material. Now referring to FIG. 3c, after APN isolation step is complete, the tubing is disengaged, and the bellows is filled with an elutant 47 (preferably, a 1M NaCl solution) to elute the APN. Next, and now referring to FIGS. 3c-3d, the threaded plug 49 of a plunger 51 is mated to the threaded end 45 of the bellows. Lastly, and now referring to FIG. 3e, the plunger is depressed and the eluted APN within the bellows is expelled from the syringe and into the osteolytic region.

Figure 4A:
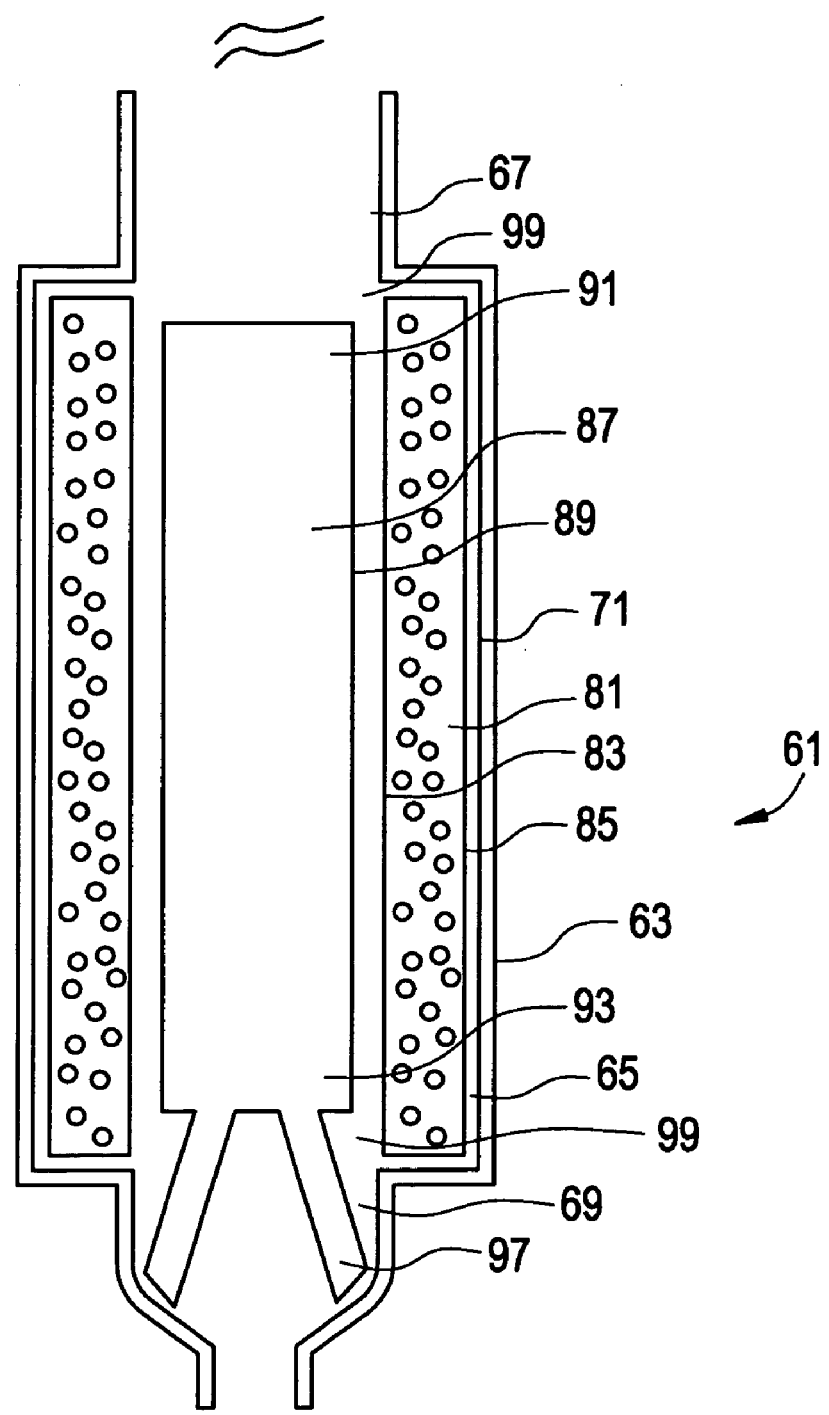
FIGS. 4a and 4b are cross-sections of a syringe of the present invention having a porous annulus adapted for separating APN from plasma.

Now referring to FIG. 4a, in some embodiments, the syringe may contain an annulus of collagen adapted for collecting APN. In particular, the apparatus 61 comprises:

a) a syringe 63 comprising a barrel 65 defining a proximal open end 67, a distal open end 69, and an inner wall 71, b) a porous annulus 81 having an inner radius 83 and an outer radius 85, the annulus adapted to be received within the inner wall of the syringe and collect APN, and c) a solid plug 87 having an outer radius 89, a proximal end 91 and a distal end 93, and adapted to be received within the inner radius of the porous annulus, and having a plurality of legs 97 extending from the distal end thereof.

In use, the plasma from the patient is run through the syringe of FIG. 4a. Since the length of the plug is less than the length of the annulus, an opening 99 is formed at each end of the barrel for convective plasma flow through the annulus.

Preferably, the porous annulus comprises of a material selected from the collagen I, collagen III, and collagen V, and mixtures thereof.

In some embodiments, monoclonal antibodies may be used to separate the adiponectin from the rest of the plasma.

After the APN is concentrated in the porous annulus, a small amount of an elutant is passed through the annulus in order to re-solubilize the APN. Preferably, the elutant is 1M NaCl.

Figure 4B:
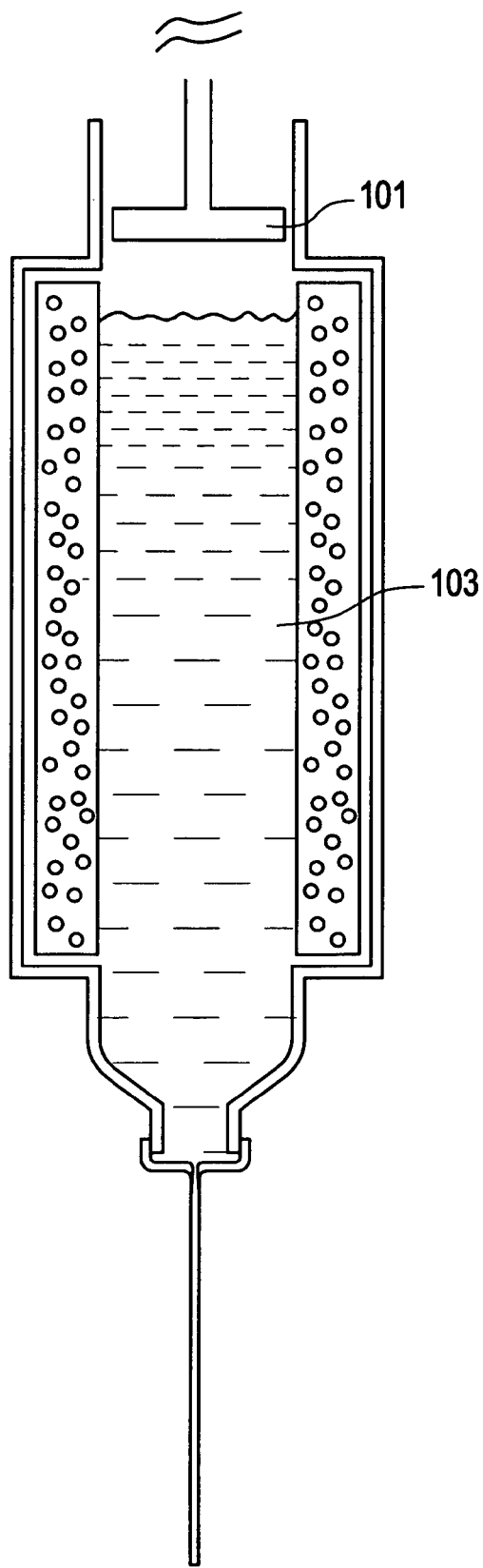

Lastly, now referring to FIG. 4b, the solid plug is removed and replaced with a plunger 101. When the plunger is depressed, APN-rich salt solution 103 is passed distally through the syringe and into the needle for delivery to the osteolytic location.

Therefore, in accordance with the present invention, there is provided an apparatus comprising:

a) a syringe comprising a barrel defining a proximal open end, a distal open end, and an inner wall, b) a porous annulus having an inner radius and an outer radius, the annulus adapted to be received within the inner wall of the syringe and collect APN.

In other embodiments, the and now referring to FIG. 5b, the porous annulus and solid plug are replaced with collagen particles 111. Plasma is passed through the particles and APN in the plasma attaches thereto. After re-solubilization of the APN with NaCl, a plunger is then placed in the syringe and depressed. The spongy nature of the collagen particles allows them to be squeezed and displaced distally, thereby pushing the APN-rich solution passed the collagen and through the distal end of the syringe.

Preferably, a mixing container is used to mix the APN and viable cells, and is adapted to provide homogeneous mixing of the APN and viable cells. In some embodiments, the container is a syringe. In other embodiments, the container is a column having a stopcock.

In embodiments in which collagen particles are used as an affinity column to separate out APN from blood or plasma, it may be desirable to simply forgo the elution step and inject both the collagen particles and the adhered APN into the patient. This procedure has advantage in that the time-consuming elution step is eliminated and the loss and/or dilution of the APN necessitated by the eluant is eliminated.

Figure 11A:
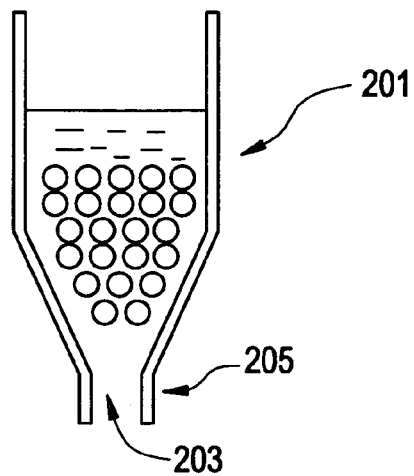
FIGS. 11a-11c are cross-sections of a syringe useful with the present invention.

Now referring to FIG. 11a, there is provided a syringe 201 having collagen particles 203 and plasma therein. In this FIG., the average diameter of the collagen particle is such that is can pass through the opening 203 in the distal end 205 of the syringe. In this particular case, the average particle size appears to be a little more than one-half the diameter of the distal opening, so that a single particle may pass through the opening, but two at a time may not. Accordingly, plasma may pass through the distal opening, but the collagen particles will quickly clog the opening.

Figure 11B:
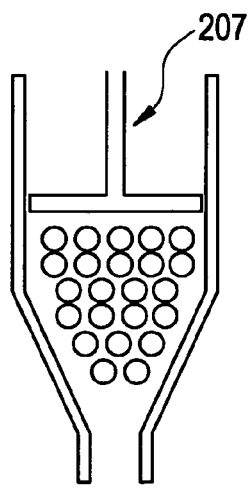

Now referring to FIG. 11b, after the plasma has been run through the syringe and APN has been adhered to the collagen particles, a plunger 207 is inserted into the syringe.

Figure 11C:
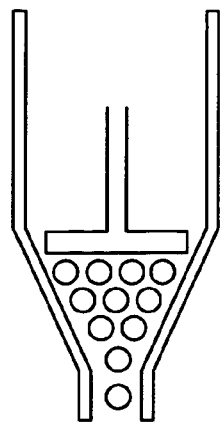

Now referring to FIG. 11c, an axial force is applied to the plunger to force the collagen particles having APN adhered thereto out of the syringe and into the patient.

In some embodiments, a dewatering agent such as a molecular sieve is provided as a coating upon a substrate. In some embodiments, the substrate can be an inner wall of a syringe or column. In others, the substrate may be in the forms of beads, such as glass or hydroxyapatite beads. In others, the substrate is organic and may be selected from agarose, hyaluronic acid and cellulose acetate.

Because, in some embodiments, the induced cells or APN are immediately injected into the patient so that the patient serves as the incubation receptacle for the induced cells, there is no need to wait for ex vivo production of IL-10 or TIMP-1. Accordingly, in preferred embodiment, the induced cells are injected into the osteolytic region less than 10 hours after the mixing step, more preferably less than 5 hours, more preferably less than three hours.

As the injection location is typically inflamed and has a local concentration of IL-1β, the APN or induced cells preferably produces an effective amount of IRAP to generate a local in vivo IRAP:IL-1β ratio of at least 1000:1, more preferably at least 10,000:1 (as measured on a molar basis).

Preferably, the APN or induced cells produced in the present invention are injected into an osteolytic region within the patient in a therapeutically effective amount. In some embodiments, the APN is injected or produced in an amount effective to reduce or eliminate inflammation present within the osteolytic region. In others, the APN is injected or produced in an amount effective to act upon nerve endings present within the osteolytic region and thereby reduce or eliminate pain.

In some embodiments, the APN is injected or produced in an amount effective to reduce or eliminate inflammation and/or pain present within the spinal cord.

In some embodiments, the APN is injected or produced in an amount effective to reduce or eliminate inflammation and/or pain present within a nerve root.

In some embodiments, the APN is injected or produced in an amount effective to reduce or eliminate inflammation associated with Alzheimer's disease within brain tissue.

In some embodiments, APN is coated upon the outside of a hydrocephalus shunt, preferably upon the ventricular catheter.

In some embodiments, APN is used (either as a coating upon a plug or per se) in repair of a hole or tear in an annulus fibrosus.

In some embodiments, APN is combined with injectable collagen such as Healos™ (available from DePuy Spine, Raynham, Mass., USA) or with Healos™—GDF-5 in order to accelerate bone regeneration after killing the pain. In some embodiments, the injectable collagen is selected from the materials disclosed in U.S. patent application USSN 10,815,000, entitled "Flowable Bone Grafts", filed Mar. 31, 2004, (Yang et al.).

EXAMPLE 1

This prophetic example describes a typical method of the present invention.

Figure 6:
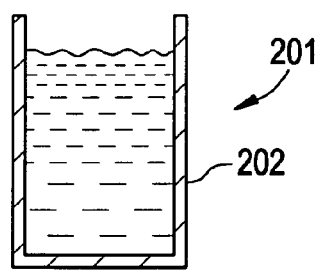
FIG. 6 is a cross-section of a centrifugation container filled with whole blood.

First, about 20 cc of blood is taken from the patient. Now referring to FIG. 6, the blood is placed in a centrifugation container 201 adapted for centrifugation and having a side wall 202.

Figure 7:
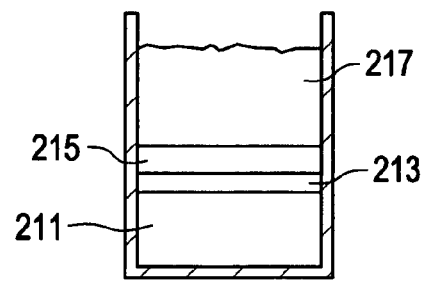
FIG. 7 is a cross-section of a centrifugation container filled with centrifuged blood.

Now referring to FIG. 7, the blood is centrifuged by a conventional method to produce centrifuged blood fractions including red blood cells 211, platelets 213, buffy coat 215 and platelet poor plasma 217.

Figure 8:
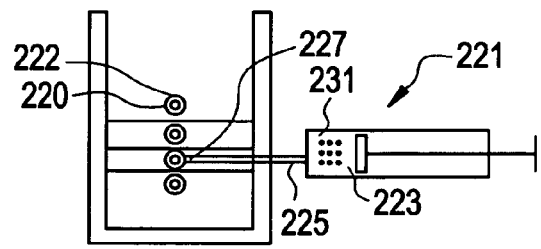
FIG. 8 is a side view of a syringe having a needle inserted into the container of FIG. 2.

Now referring to FIG. 8, a syringe 221 having a barrel 223 and a needle 225 is provided. The centrifugation container has a plurality of side ports 220 having puncturable gaskets 222 therein. The clinician inserts the distal end 227 of the needle through a gasket.

Figure 9:
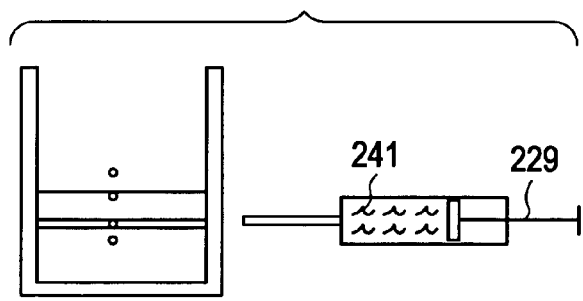
FIG. 9 is a side view of a syringe filled with APN-rich plasma.

Now referring to FIG. 9, the clinician pulls back upon the plunger 229. The vacuum created by withdrawl of the plunger causes the APN-containing fluid to enter the barrel of the syringe. Molecular sieve beads contained within the barrel of the syringe pull water from the fluid, thereby creating an APN-rich fluid.

Next, the clinician uses a diagnostic test to verify that the periprosthetic region within a patient has high levels of the particular interleukin-1β pro-inflammatory cytokine, MMP-1 or TNF-α.

Next, the clinician provides a local anesthetic (such as 5 ml lidocaine) to the periprosthetic region of concern to reduce subcutaneous pain.

Next, the clinician punctures the skin of the patient with a relatively large (e.g., 18-19 gauge) needle having a stylet therein, and advances the needle through subcutaneous fat, ligament and muscles to the osteolytic region.

Next, the stylet is removed from the needle.

Next, the clinician receives the syringe having the inducing composition of the present invention. This syringe has a smaller gauge needle adapted to fit within the larger gauge needle. This smaller needle is typically a 22 or 24 gauge needle. The barrel of the syringe contains the formulation of the present invention.

Figure 10:
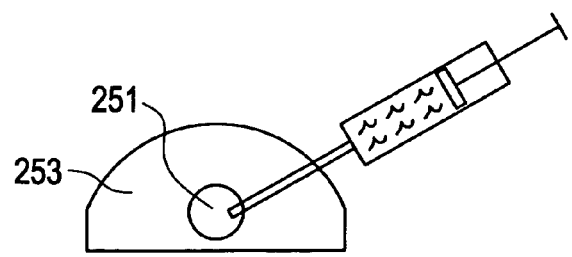
FIG. 10 is a cross-section of a syringe of the present invention injecting APN-rich plasma into an osteolytic region.

Finally, and now referring to FIG. 10, the clincian depresses the plunger of the syringe, thereby injecting between about 0.5 and 1 ml of the formulation comprising an effective amount of APN into the osteolytic region 251 adjacent a prosthetic acetabular cup 253.

We claim:

1. A method of inhibiting osteolysis comprising periprosthetically administering to a patient in need thereof an effective amount of a formulation comprising autologous adiponectin and a carrier into an osteolytic region of said patient, wherein the administration includes local injection of the formulation through a needle into the osteolytic region,
   wherein the adiponectin is obtained from blood of the patient,
   wherein the adiponectin is contained in a formulation consisting essentially of the carrier and plasma.

2. The method of claim 1 wherein the adiponectin is exogenous.

3. The method of claim 1 wherein the osteolytic region is associated with a hip joint prosthesis.

4. The method of claim 3 wherein the osteolytic region is associated with an acetabular cup in the hip joint prosthesis.

5. The method of claim 1 wherein the osteolytic region is associated with a knee joint prosthesis.

6. The method of claim 1 wherein the osteolytic region is associated with an intervertebral motion disc prosthesis.

7. The method of claim 1 wherein the APN combines with native macrophages within the osteolytic region to produce an amount of IL-10 effective to treat osteolysis.

8. The method of claim 1 wherein the formulation comprises at least 5 μg APN/ml.

9. The method of claim 1 wherein the formulation comprises at least 10 μg APN/ml.

10. The method of claim 1 wherein the formulation comprises at least 20 μg APN/ml.

* * * * *